United States Patent
Durr et al.

(10) Patent No.: US 9,717,705 B2
(45) Date of Patent: Aug. 1, 2017

(54) ANAPLEROTIC THERAPY OF HUNTINGTON DISEASE AND OTHER POLYGLUTAMINE DISEASES

(71) Applicant: INSERM (Institut National de la Sante et de la Recherche Medicale), Paris (FR)

(72) Inventors: Alexandra Durr, Paris (FR); Fanny Mochel, Saint Maur des Fosses (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 14/308,966

(22) Filed: Jun. 19, 2014

(65) Prior Publication Data

US 2014/0364498 A1 Dec. 11, 2014

Related U.S. Application Data

(63) Continuation of application No. 13/341,028, filed on Dec. 30, 2011, now abandoned, which is a continuation of application No. 12/516,486, filed as application No. PCT/EP2007/063181 on Dec. 3, 2007, now abandoned.

(30) Foreign Application Priority Data

Dec. 4, 2006 (EP) ................... 06291873

(51) Int. Cl.
| | | |
|---|---|---|
| *A61K 31/225* | (2006.01) | |
| *A23L 29/00* | (2016.01) | |
| *A23L 33/115* | (2016.01) | |
| *A23L 33/12* | (2016.01) | |

(52) U.S. Cl.
CPC ............ *A61K 31/225* (2013.01); *A23L 29/04* (2016.08); *A23L 33/115* (2016.08); *A23L 33/12* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 4,025,649 A | 5/1977 | Taillandier et al. | |
| 4,753,963 A | 6/1988 | Jandacek | |
| 6,335,361 B1 | 1/2002 | Hamilton | |
| 6,740,679 B1 | 5/2004 | Roe | |
| 6,835,750 B1 | 12/2004 | Henderson | |
| 8,399,515 B2 | 3/2013 | Roe | |
| 9,468,229 B2 | 10/2016 | Mochel et al. | |
| 2006/0004099 A1 | 1/2006 | Roe | |
| 2006/0189545 A1 | 8/2006 | Henderson et al. | |
| 2007/0123588 A1 | 5/2007 | Charles | |
| 2008/0085920 A1 | 4/2008 | Donello et al. | |
| 2008/0132571 A1 | 6/2008 | Roe | |
| 2008/0287372 A1 | 11/2008 | Henderson | |
| 2009/0253781 A1 | 10/2009 | Veech | |
| 2010/0063147 A1 | 3/2010 | Durr et al. | |
| 2011/0201558 A1 | 8/2011 | Roe et al. | |
| 2011/0301238 A1 | 12/2011 | Borges | |
| 2011/0306663 A1 | 12/2011 | Schiffmann et al. | |
| 2012/0164243 A1 | 6/2012 | Rinsch et al. | |
| 2012/0165405 A1 | 6/2012 | Durr et al. | |
| 2013/0123359 A1 | 5/2013 | Roe | |
| 2014/0221482 A1 | 8/2014 | Mochel et al. | |
| 2016/0263071 A1 | 9/2016 | Borges et al. | |
| 2016/0374980 A1 | 12/2016 | Mochel et al. | |

FOREIGN PATENT DOCUMENTS

| | | |
|---|---|---|
| DE | 3032300 A1 | 4/1982 |
| EP | 1929995 | 6/2008 |
| GB | 2104079 A | 3/1983 |
| KR | 10-2001-0108173 | 12/2001 |
| PH | H6-287138 | 10/1994 |
| WO | 00/45649 | 8/2000 |
| WO | WO 0045649 A1 * | 8/2000 |
| WO | WO 01/82928 | 11/2001 |
| WO | 2004/077938 | 9/2004 |
| WO | WO 2004077938 A2 * | 9/2004 |
| WO | WO 2004/103307 | 12/2004 |
| WO | 2006/189545 | 8/2006 |
| WO | WO 2008/068230 | 6/2008 |
| WO | WO 2009/018478 | 2/2009 |
| WO | WO 2009/124250 | 10/2009 |
| WO | WO 2011/082111 | 7/2011 |
| WO | WO 2011/159634 | 12/2011 |
| WO | WO 2015/073803 | 5/2015 |

OTHER PUBLICATIONS

Henderson et al. ("Henderson", of record) further in view of Kinman et al., "Parenteral and enteral metabolism of anaplerotic triheptanoin in normal rats", Am. J. Physiol. Endocrinol. Metab., 291(4):E860-E866 (2006).*
Roe et al., Treatment of cardiomyopathy and rhabdomyolysis in long-chain fat oxidation disorders using an anaplerotic odd-chain triglyceride, J Clin Invest. Jul. 2002;110(2):259-69.*
Veech et al, 2001, IUBMB Life 51: 241-247.*
Aso et al., Current Alzheimer Research 10: 290-297, 2013.*
Antonini et al., "Striatal glucose metabolism and dopamine D2 receptor binding in asymptomatic gene carriers and patients with Huntington's disease," Brain, 119(Pt 6):2085-2095 (1996).
Beal, "Neurochemical and histologic characterization of striatal excitotoxic lesions produced by the mitochondrial toxin 3-nitropropionic acid," J. Neurosci., 13:4181-4192 (1993).
De Bandt et al., "Therapeutic use of branched-chain amino acids in burn, trauma, and sepsis," J. Nutr., 136(1 Suppl):308S-313S (2006).
Ferrante, "Neuroprotective effects of creatine in a transgenic mouse model of Huntington's disease," J. Neurosci., 20:4389-4397 (2000).
Kinman et al., "Parenteral and enteral metabolism of anaperotic triheptanonin in normal rats," Am. J. Physiol. Endocrinol. Metab., 291(4):E860-E866 (2006).

(Continued)

*Primary Examiner* — Svetlana M Ivanova

(74) *Attorney, Agent, or Firm* — Cooley LLP

(57) ABSTRACT

The present invention relates to a method for treating and/or preventing Huntington disease and other polyglutamine diseases, comprising the step of administering an effective amount of a precursor of propionyl-CoA to an individual in need thereof.

8 Claims, 6 Drawing Sheets

(56) References Cited

OTHER PUBLICATIONS

Figure 1:
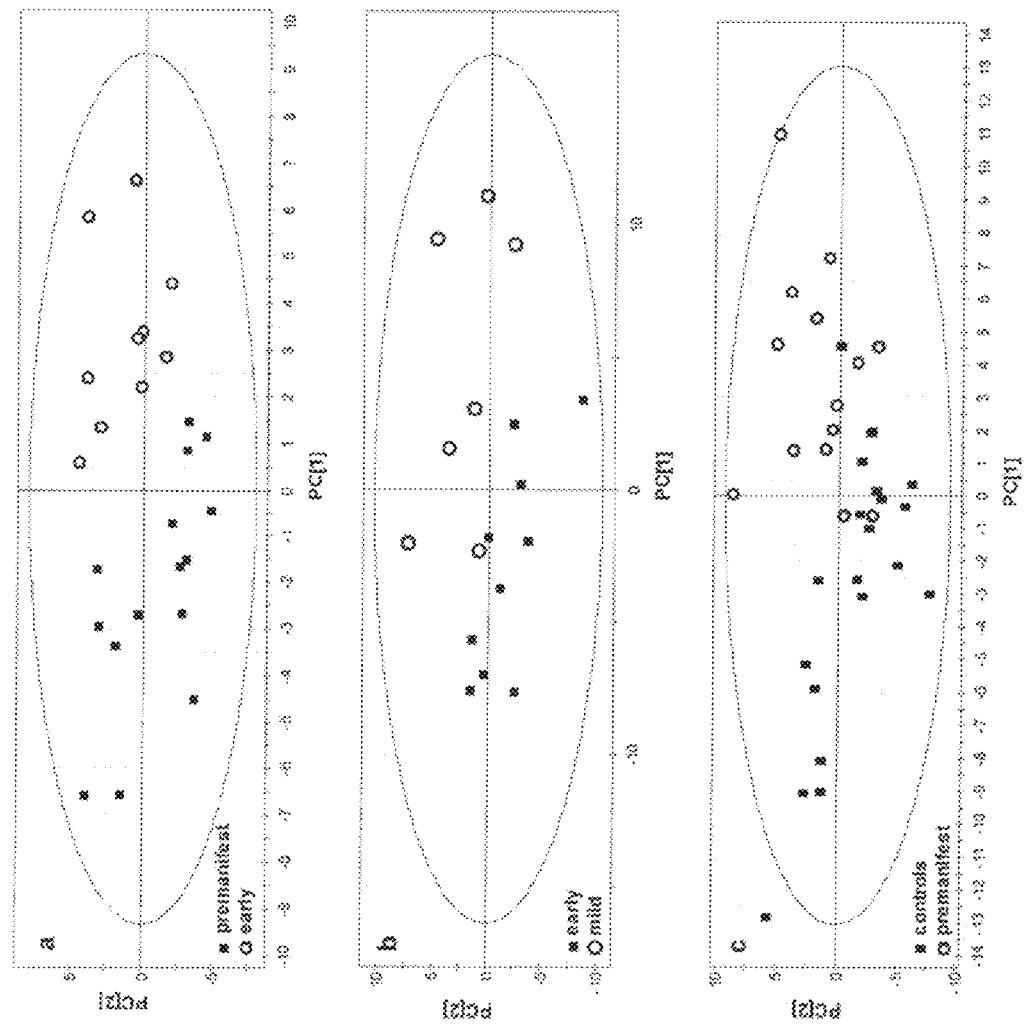

Milakovic et al., "Mitochondrial respiration and ATP production are significantly impaired in striatal cells expressing mutant huntingtin," J. Biol. Chem., 280(35):30773-30782 (2005).
Mochel et al., "Early energy deficit in Huntington disease: identification of a plasma biomarker traceable during disease progression," Plos One, 2(7):e647 (2007).
Rangone et al., "Phosphorylation of arfaptin 2 at Ser260 by Akt Inhibits PolyQ-huntingtin-induced toxicity by rescuing proteasome impairment," J. Biol. Chem., 280(23):22021-22028 (2005).
Reszko et al., "Assessing the reversibility of the anaplerotic reactions of the propionyl-CoA pathway in heart and liver," J. Biol. Chem., 278:34959-34965 (2003).
Roe et al., "Treatment of cardiomyopathy and rhabdomyolysis in long-chain fat oxidation disorders using an anaplerotic odd-chain triglyceride," J. Clin. Invest., 110(2):259-269 (2002).
Sabatine et al., "Metabolomic identification of novel biomarkers of myocardial ischemia," Circulation, 112(25):3868-3875 (2005).
Segal et al., "Lean body mass estimation by bioelectrical impedance analysis: a four-site cross-validation study," Am. J. Clin. Nutr., 47(1):7-14 (1988).
Underwood, "Huntington disease patients and transgenic mice have similar pro-catabolic serum metabolite profiles," Brain, 129:877-886 (2006).
Walsh et al., "Effect of acute dietary standardization on the urinary, plasma, and salivary metabolomic profiles of healthy humans," Am. J. Clin. Nutr., 84(3):531-539 (2006).
Guy, D., et al., "Effect of Diets High in Carbohydrate, Soy Oil, Medium-Chain Triglycerides or Tripelargonin on Blood and Liver Lipid and Glucose Intermediates in Meal-Eating Rats," *J. of Nutrition* 111: 1437-1445, 1981.
Deng, S., et al., "Interrelations between $C_4$ Ketogenesis, $C_5$ Ketogenesis, and Anaplerosis in the Perfused Rat Liver," *J. Biol. Chem.* 284(41): 27799-27807, 2009.
Henderson, S., et al., "Study of the Ketogenic Agent AC-1202 in Mild to Moderate Alzheimer's Disease: A Randomized, Double-Blind, Placebo-Controlled, Multicenter Trial," *Nutrition & Metabolism* 6: 31, 2009.
Aso, E., et al., "Triheptanoin Supplementation to Ketogenic Diet Curbs Cognitive Impairment in APP/PS1 Mice Used as a Model of Familial Alzheimer's Disease," *Current Alzheimer's Research* 10: 290-297, 2013.
Vlaeminck et al. "Milk Odd- and Branched-Chain Fatty Acids in Relation to the Rumen Fermentation Pattern", *Journal of Dairy Science*, 89(10):3954-3964, Oct. 1, 2006.
European Search Report based on European Patent Application No. EP15175719.2, mailed on Feb. 3, 2016.
Supplementary European Search Report and Written Opinion for European Application No. 10841613.2, mailed Jun. 4, 2013, 10 pages.
International Search Report and Written Opinion for International Application No. PCT/US2010/062054, mailed Feb. 23, 2011, 9 pages.
Supplementary European Search Report and Written Opinion for European Application No. 13862044.8, mailed Jun. 29, 2016, 7 pages.
International Search Report and Written Opinion for International Application No. PCT/US2013/075146, mailed Mar. 11, 2014, 9 pages.
International Search Report and Written Opinion for International Patent Application No. PCT/US2014/065670, mailed Feb. 12, 2015, 11 pages.
Supplemental European Search Report for European Application No. 06291873.5, mailed Jun. 12, 2007, 9 pages.
International Search Report and Written Opinion for International Application No. PCT/EP2007/063181, mailed Apr. 21, 2008, 10 pages.

Andreassen, O. A. et al., "Dichloroacetate exerts therapeutic effects in transgenic mouse models of Huntington's disease," Annals of Neurology, 50(1):112-117 (Jul. 2001).
Beal, M. F., "Energetics in the pathogenesis of neurodegenerative diseases," Trends in Neurosciences, 23(7):298-304 (Jul. 2000).
Bjorkqvist, M. et al., "The R6/2 transgenic mouse model of Huntington's disease develops diabetes due to deficient b-cell mass and exocytosis," Human Molecular Genetics, 2005, 14(5):565-574, doi:10.1093/hmg/ddi053, Advance Access published on Jan. 13, 2005.
Boesgaard, T. W. et al., "Huntington's Disease does not appear to increase the risk of diabetes mellitus," Journal of Neuroendocrinology, vol. 21, Issue 9, Sep. 2009, pp. 770-776.
Borges, K. et al. "Gene expression changes after seizure preconditioning in the three major hippocampal cell layers," Neurobiology of Disease, 26:66-77 (Jan. 2007).
Borges, K. et al., "Triheptanoin—a medium chain triglyceride with odd chain fatty acids: A new anaplerotic anticonvulsant treatment?", Epilepsy Research, 100(3):239-244 (2011).
Borges, K. et al., "Anti-Epileptic Effects of Triheptanoin in Two Chronic Mouse Epilepsy Models," presented at the 24th Annual Scientific Meeting, Epilepsy Society of Australia, Perth Convention Exhibition Center (Nov. 2-4, 2009).
Borges, Slides Presented at the International Symposium on Dietary Therapies for Epilepsy and Other Neurological Disorders in Phoenix, Arizona on Mar. 8, 2008.
Borges, Slides Printed and Distributed at the International Symposium on Dietary Therapies for Epilepsy and Other Neurological Disorders in Phoenix, Arizona on Mar. 8, 2008.
Breen, C., "Unsuccessful treatment of severe pyruvate carboxylase deficiency with triheptanoin," Eur. J. Pediatr., 173:361-366 (2014).
Brockmann, K., "The expanding phenotype of GLUT1-deficiency syndrome," Brain & Development, 31:545-552 (2009).
Brunengraber, H. et al., "Anaplerotic molecules: current and future," J Inherit Metab Dis., 29:327-331 (2006).
Buckner, R. L. et al., "The Brain's Default Network, Anatomy, Function, and Relevance to Disease," Ann. N.Y. Acad. Sci., 1124:1-38 (2008).
Clarke, D. D. et al., "Circulation and energy metabolism of the brain," Chapter 31 in: Siegel G. J. et al. (eds.), Basic Neurochemistry: Molecular, Cellular and Medical Aspects, 6th edition, Philadelphia: Lippincott-Raven, 638-669 (1999).
de Almeida Rabello Oliveira et al., "Effects of short-term and long-term treatment with medium- and long-chain triglycerides ketogenic diet on cortical spreading depression in young rats," Neuroscience Letters, 434:66-70 (2008).
Farrer, L. A., "Diabetes mellitus in Huntington disease," Clinical Genetics 1985, 27:62-67.
Freeman, J. M. et al., "Ketosis and the ketogenic diet, 2010: advances in treating epilepsy and other disorders," Advances in Pediatrics, 57:315-329 (2010).
Gabuzda, D. et al., "Inhibition of energy metabolism alters the processing of amyloid precursor protein and induces a potentially amyloidogenic derivative," The Journal of Biological Chemistry, 269(18):13623-13628.
Glenner, G. G et al., "The amyloid deposits in Alzheimer's disease: their nature and pathogenesis," Appl. Pathol., 2(6):357-369 (1984).
Goedert, M. et al., "Cloning and sequencing of the cDNA encoding a core protein of the paired helical filament of Alzheimer disease: Identification as the microtubule-associated protein tau," Proc. Natl. Acad. Sci. USA, 85(11):4051-4055 (1988).
Graham, J. M. Jr., "GLUT1 deficiency syndrome as a cause of encephalopathy that includes cognitive disability, treatment-resistant infantile epilepsy and a complex movement disorder," Eur J Med Genet., 55(5):232-234 (May 2012).
Grundke-Iqbal, I. et al., "Abnormal Phosphorylation of the Microtubule-Associated Protein (tau) in Alzheimer Cytoskeletal Pathology," Proc. Natl. Acad, Sci., 83(13):4913-4917 (1986).
Hardy, J. A. et al., "Alzheimer's disease: the amyloid cascade hypothesis," Science, 256(5054):184-185 (Apr. 1992).
Henderson, S. T., "Ketone bodies as a therapeutic for Alzheimer's disease," Neurotherapeutics, 5(3):470-480 (Jul. 2008).

(56) References Cited

OTHER PUBLICATIONS

Hurlbert, M. S. et al., "Mice transgenic for an expanded CAG repeat in the Huntington's Disease gene develop diabetes," Diabetes Mar. 1999; 48(3): 649-651. https://doi.org/10.2337/diabetes.48.3.649.
IP High Court Case No. Heisei 21 (Gyoke) 10033, decided on Jan. 28, 2010, Brief History of the case, pp. 14-17.
Kashiwaya, Y. et al., "D-β-Hydroxybutyrate protects neurons in models of Alzheimer's and Parkinson's disease," PNAS, 97(10):5440-5444 (May 2000).
Klepper, J. et al., "GLUT1 deficiency syndrome—2007 update," Dev Med Child Neurol., 49:707-716 (2007).
Klepper, J., "GLUT1 deficiency syndrome in clinical practice," Epilepsy Research, 100(3):272-277 (2012).
Kudin, A. P. et al., "Mitochondrial involvement in temporal lobe epilepsy," Experimental Neurology, 218:326-332 (2009).
Lalic, N. M. et al., "Glucose homeostasis in Huntington Disease. Abnormalities in insulin sensitivity and early-phase insulin secretion," Arch Neurol. 2008;65(4):476-480.
Leen, W. G. et al., "Glucose transporter-1 deficiency syndrome: the expanding clinical and genetic spectrum of a treatable disorder," Brain, 133(3):655-670 (2010).
Loscher, W., "Critical review of current animal models of seizures and epilepsy used in the discovery and development of new antiepileptic drugs," Seizure, 20:359-368 (2011).
Marin-Valencia, I. et al., "Heptanoate as a neural fuel: energetic and neurotransmitter precursors in normal and glucose transporter I-deficient (G1D) brain," Journal of Cerebral Blood Flow & Metabolism, 33(2):175-182 (2013).
Masters, C. L. et al., "Amyloid Plaque Core Protein in Alzheimer Disease and Down Syndrome," Proc. Natl. Acad. Sci., 82(12):4245-4249 (Jun. 1985).
McDonald, T. S. et al., "Alterations of hippocampal glucose metabolism by even versus uneven medium chain triglycerides," Journal of Cerebral Blood Flow & Metabolism (2014) 34, 153-160.
Mochel, F. et al., "Dietary anaplerotic therapy improves peripheral tissue energy metabolism in patients with Huntington's disease," European Journal of Human Genetics, 18:1057-1060 (2010).
Mochel, F. et al., "Pyruvate carboxylase deficiency: clinical and biochemical response to anaplerotic diet therapy," Molecular Genetics and Metabolism, 84:305-312 (2005).
Mosconi, L. et al., "Brain Glucose Hypometabolism and Oxidative Stress in Preclinical Alzheimer's Disease," Ann N Y Acad Sci. Dec. 2008; 1147:180-195. doi:10.1196/annals.1427.007.
Neal, E. G. et al., "A randomized trial of classical and medium-chain triglyceride ketogenic diets in the treatment of childhood epilepsy," Epilepsia, 50(5):1109-1117 (May 2009).
Pascual, J., "GLUT1 Transporter Deficiency Syndrome Conference," Clinical Research, Louisville, Kentucky, Jul. 15, 2010, Glut1 DS Conference, 21 pages.
Pascual, J. M. et al., "Brain glucose supply and the syndrome of infantile neuroglycopenia," Archives of Neurology, 64(4):507-513 (Apr. 2007).
Perlman, B. J. et al., "Membrane-disordering potency and anticonvulsant action of valproic acid and other short-chain fatty acids," Molecular Pharmacology, 26:83-89 (1984).
Podolsky, S. et al., "Increased frequency of diabetes mellitus in patients with Huntington's chorea," The Lancet, vol. 299, Issue 7765, Jun. 24, 1972, pp. 1356-1359. Originally published as vol. 1, Issue 7765.
Pong, A. W. et al., "Glucose transporter type I deficiency syndrome: Epilepsy phenotypes and outcomes" Epilepsia, 53(9):1503-1510 (2012).
Reger, M. A. et al., "Effects of β-hydrozybutyrate on cognition in memory-impaired adults," Neurobiology of Aging, 25(3):311-314 (2004).
Roe, C. R. et al., "Anaplerotic diet therapy in inherited metabolic disease: therapeutic potential," Journal of Inherited Metabolic Disease, 29(2-3):332-340 (Apr.-Jun. 2006).
Roe, C. R. et al., "Carnitine palmitoyltransferase II deficiency: successful anaplerotic diet therapy," Neurology, 71:260-264 (2008).
Schneider, S. A. et al., "GLUT1 gene mutations cause sporadic paroxysmal exercise-induced dyskinesias," Movement Disorders, 24(11):1684-1688 (2009).
Seidner, G. et al., "GLUT-1 deficiency syndrome caused by haploinsufficiency of the blood-brain barrier hexose carrier," Nat Genet., 18:188-191 (1998).
Seyfried, T. N. et al., "Ketone strong: Emerging evidence for a therapeutic role of ketone bodies in neurological and neurodegenerative diseases," Journal of Lipid Research, 55:1815-1817 (2014).
Stafstrom, C. E. et al., "The ketogenic diet as a treatment paradigm for diverse neurological disorders," Frontiers in Pharmacology, vol. 3, Article 59, pp. 1-8 (Apr. 2012).
Stepan Company, NEOBEE 895, Overview (2012), 3 pages (online), Retrieved from the Internet: <URL: http://www.stepan.com/Products/Specialty-Products/NEOBEE/NEO . . . >, Retrieved on: Jan. 21, 2015.
Striano, P. et al., "GLUT1 mutations are a rare cause of familial idiopathic generalized epilepsy," Neurology, 78:557-562 (2012).
Thomas, N. K. et al., "Triheptanoin in acute mouse seizure models," Epilepsy Research, 99:312-317 (2012).
Van Der Auwera, I. et al., "A ketogenic diet reduces amyloid beta 40 and 42 in a mouse model of Alzheimer's disease," Nutrition & Metabolism, 2:28 (2005).
Velliquette, R. A., et al., "Energy inhibition elevates β-secretase levels and activity and is potentially amyloidogenic in APP transgenic mice: Possible early events in Alzheimer's disease pathogenesis," The Journal of Neuroscience, 25(47):10874-10883 (2005).
Verrotti, A. et al., "Glut1 deficiency: When to suspect and how to diagnose?" Eur. J. Paedeatr. Neurol., 16:3-9 (2012).
Wang, D. et al., "Glut-1 deficiency syndrome: clinical, genetic, and therapeutic aspects," Ann Neurol., 57:111-118 (2005).
Wang, X. et al., "Anaplerosis from heptanoate-a propionyl-CoA precursor- in mouse brain," The FASEB Journal, 21:541.12 (2007) (Abstract).
White, H. S., "Preclinical Development of Antiepileptic Drugs: Past, Present, and Future Directions," Epilepsia, 44(7):2-8 (2003).
Wikipedia, Definition of "Axona," [Retrieved on Feb. 9, 2013], Retrieved from the Internet: <URL: http://en.wikipedia/org/wiki/Axona>, 3 pages.
Wikipedia, Definition of "Fatty Acid," [Retrieved on Oct. 13, 2016], Retrieved from the Internet: <URL: https://en.wikipedia/org/wiki/Fatty_Acid>, 7 pages.
Willis, S. et al., "Anticonvulsant effects of a triheptanoin diet in two mouse chronic seizure models," Neurobiology of Disease, 40(3):565-572 (2010).
Willis, S. et al., "The effect of anaplerotic diet in mouse epilepsy models," Presentation Abstract, Program#/Poster #: 539.8/P4, Neuroscience Meeting Planner, Chicago, IL: Society for Neuroscience (2009).
Zhao, W. et al., "Caprylic triglyceride as a novel therapeutic approach to effectively improve the performance and attenuate the symptoms due to the motor neuron loss in ALS disease," PloS ONE 7(11):e49191 (2012). doi:10.1371/journal.pone.0049191.

* cited by examiner

ANAPLEROTIC THERAPY OF HUNTINGTON DISEASE AND OTHER POLYGLUTAMINE DISEASES

The present application is filed as a continuation of U.S. patent application Ser. No. 13/341,028, filed Dec. 30, 2011, which is a continuation of U.S. patent application Ser. No. 12/516,486, which was filed May 27, 2009, which was filed pursuant to 35 U.S.C. 371 as a U.S. National Phase application of International Patent Application No. PCT/EP07/63181, which was filed Dec. 3, 2007, claiming the benefit of priority to European Patent Application No. 06291873.5, which was filed on Dec. 4, 2006. The entire text of the aforementioned applications is incorporated herein by reference in its entirety.

FIELD OF THE INVENTION

The present invention relates to the treatment and the prevention of Huntington disease and other polyglutamine diseases.

BACKGROUND OF THE INVENTION

Huntington disease (HD) is a devastating inherited neurodegenerative disease without curative treatment. HD is the founding member of a large group of diseases due to polyglutamine accumulation and toxicity. There is a critical need for new insights in the pathophysiology of this disease, as well as for the identification of relevant molecules for clinical trials.

Several observations have led to the hypothesis that mitochondrial dysfunction has a role in polyglutamine diseases, and in Huntington disease in particular. Several lines of evidence indicate abnormal energy metabolism, including reduced glucose metabolism, elevated lactate levels and impaired mitochondrial-complex activity (Di Prospero and Fischbeck 2005, Nat Rev Genet 6(10): 756-65). To explain this abnormal energy metabolism most studies favoured a secondary impairment of the mitochondrial respiratory chain. An important decrease in complexes II & III (55%) has been shown in the caudate of HD patients (Gu 1996, Ann Neurol 39: 385-9), as well as a deficiency in complex I in muscle (Arenas 1998, Ann Neurol 43: 397-400), therefore supporting the possibility of mitochondrial respiratory chain defects in pathogenesis of HD (Shapira 1998, Biochem Biophys Acta 1366: 225-33, Grunewald 1999, Ann N Y Acad Sci 893: 203-13). These findings correlated with HD models induced by 3-nitropropionic acid, an irreversible complex II inhibitor (Beal 1993, J Neurosci 13: 4181-92). However, these data are controverted by the demonstration of normal mitochondrial electron transport complexes in transgenic mice at an early stage (Guidetty 2001, Exp Neurol 169: 340-50), as well as in striatal cells in culture expressing mutant huntingtin, despite the significant reduction in ATP synthesis observed in those cells (Milakovic 2005, JBC 280: 30773-82). Additional indirect evidence for an energy defect in polyglutamine diseases arise from the partial efficacy of energetic therapies, such as dichloroacetate (Andreassen 2001, Ann Neurol 50: 112-9), pyruvate (Ryu 2004, Exp Neurol 187: 150-9), creatine (Ferrante 2000, J Neurosci 20: 4389-97) and coenzyme Q10 (Schilling 2001, Neurosci Lett 315: 149-53) in mice models.

However, to date, effective pharmacotherapy for neurodegenerative diseases associated with impaired energy metabolism like polyglutamine diseases in particular, remains rather elusive.

SUMMARY OF THE INVENTION

Therefore, it is an object of the present invention to provide a method for treating and/or preventing polyglutamine disease such as Huntington disease.

In fulfilling this object, there is provided a method for treating and/or preventing a polyglutamine disease, comprising the step of administering an effective amount of a precursor of propionyl-CoA to an individual in need thereof.

Also provided is the use of a precursor of propionyl-CoA in the manufacture of a medicament for treating and/or preventing polyglutamine disease.

DETAILED DESCRIPTION OF THE INVENTION

The present invention provides a method for treating and/or preventing a polyglutamine disease, comprising the step of administering an effective amount of a precursor of propionyl-CoA to an individual in need thereof.

By individual, it is meant animal or human being.

Also provided is a precursor of propionyl-CoA for treating and/or preventing a polyglutamine disease.

Also provided is the use of a precursor of propionyl-CoA in the manufacture of a medicament and/or a food substance for treating and/or preventing a polyglutamine disease.

Polyglutamine diseases constitute a class of nine genetically distinct disorders that are caused by expansion of translated CAG repeat. These include Huntington disease (HD), dentatorubralpallidoluysian atrophy (DRPLA), spinal and bulbar muscular atrophy (SBMA) and spinocerebellar ataxia 1, 2, 3, 6, 7 and 17. Although the disease causing proteins are expressed widely in the central nervous system, specific populations of neurons are vulnerable in each disease, resulting in characteristic patterns of neurodegeneration and clinical features.

In an embodiment of the present invention, the polyglutamine disease is selected from the group consisting of Huntington disease (HD), dentatorubralpallidoluysian atrophy (DRPLA), spinal and bulbar muscular atrophy (SBMA), spinocerebellar ataxia 1, 2, 3, 6, 7 and 17.

In a preferred embodiment of the present invention, the polyglutamine disease is Huntington disease.

By precursor of propionyl-CoA, it is meant a substance from which propionyl-CoA can be formed by one or more metabolic reactions taking place within the body.

Figure 5:
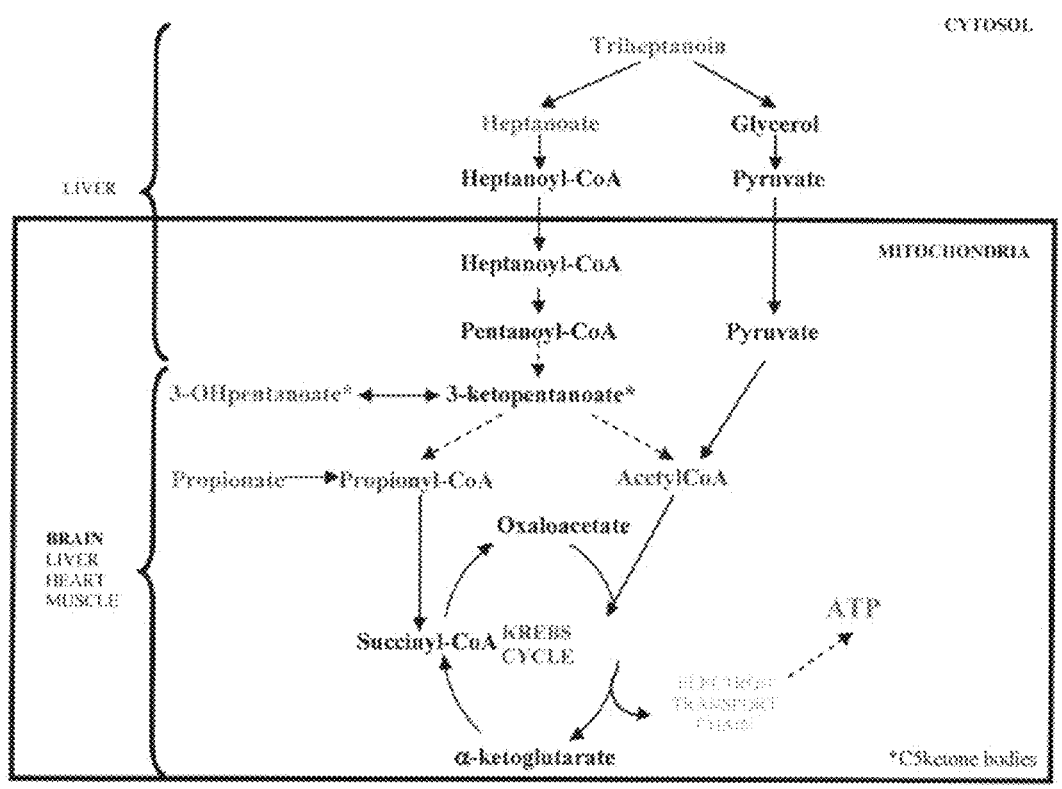

Examples of precursors of propionyl-CoA are shown in FIG. 5. Typical examples of precursors of propionyl-CoA are odd-medium-chain fatty acids, in particular seven-carbon fatty acid, triheptanoin (triheptanoyl-glycerol), heptanoate, C5 ketone bodies (e.g. β-ketopentanoate (3-ketovalerate), and β-hydroxypentanoate (3-hydroxyvalerate)) (Kinman 2006, Am J Physiol Endocrinol Metab 291 (4): E860-6, Brunengraber and Roe 2006, J Inherit Metabol Dis 29 (2-3): 327-31).

The examples of precursors of propionyl-CoA described above include the compounds themselves, as well as their salts, prodrugs, solvates, if applicable. Examples of prodrugs include esters, oligomers of hydroxyalkanoate such as oligo (3-hydroxyvalerate) (Seebach 1999, Int J Biol Macromol 25 (1-3): 217-36) and other pharmaceutically acceptable derivatives, which, upon administration to a individual, are capable of providing propionyl-CoA. A solvate refers to a complex formed between a precursor of propionyl-CoA described above and a pharmaceutically acceptable solvent.

Examples of pharmaceutically acceptable solvents include water, ethanol, isopropanol, ethyl acetate, acetic acid, and ethanolamine.

A very practical dietary source of propionyl-CoA is triheptanoin (triheptanoyl-glycerol). After intestinal hydrolysis of triheptanoin, heptanoate is absorbed in the portal vein. In the liver, it is partially converted to the C5 ketone bodies β-ketopentanoate (3-ketovalerate), and β-hydroxypentanoate (3-hydroxyvalerate). The C5-ketones bodies are also precursors of propionyl-CoA in peripheral tissues. Thus, after ingestion of triheptanoin, peripheral tissues receive two precursors of propionyl-CoA, i.e., heptanoate and C5-ketone bodies. Quite interestingly, C5-, like C4-, ketone bodies are natural substrates for the brain and can target physiological receptors at the surface membrane of the blood brain barrier. The demonstration of the transport of C5-ketone bodies across the blood-brain barrier was recently provided by the treatment of a patient with pyruvate carboxylase deficiency, where cerebral anaplerosis is primarily impaired (Mochel 2005, Mol Genet Metab 84: 305-12). The availability of C5-ketone bodies for cerebral anaplerosis was also demonstrated by the normalisation of glutamine and GABA in the CSF of this patient, as well as the absence of brain pathology.

The person skilled in the art is aware of standard methods for production of precursors of propionyl-CoA.

In a preferred embodiment of the present invention, the precursor of propionyl-CoA is triheptanoin, heptanoic acid or heptanoate.

Triheptanoin has already been used in the anaplerotic treatment of a few pathologies having in common a decrease in ATP production in spite of ample supply of acetyl-CoA to the citric acid cycle (CAC), and a normal respiratory chain. Such pathologies include cardiac reperfusion injury (Reszko 2003, JBC 278: 34959-65), long-chain fatty acid oxidation disorders (FOD) (Roe 2002, JCI 110: 259-69 and WO 0045649), pyruvate carboxylase deficiency (Mochel 2005, Mol Genet Metab 84: 305-12) and glycogen storage disease type II (Roe and Mochel 2006, J Inherit Metab Dis 29 (2-3): 332-40)

Triheptanoin is a triglyceride made by the esterification of three n-heptanoic acid molecules and glycerol. In regard to therapy, the terms heptanoic acid, heptanoate, and triheptanoin may be used interchangeably in the following description. Also, it will be understood by one skilled in the art that heptanoic acid, heptanoate, and triheptanoin are exemplary precursors of propionyl-CoA of the invention. Substituted, unsaturated, or branched heptanoate, as well as other modified seven-carbon fatty acids can be used without departing from the scope of the invention.

Heptanoic acid is found in various fusel oils in appreciable amounts and can be extracted by any means known in the art. It can also be synthesized by oxidation of heptaldehyde with potassium permanganate in dilute sulfuric acid (Ruhoff, Org Syn Coll. vol II, 315 (1943)). Heptanoic acid is also commercially available through Sigma Chemical Co. (St. Louis, Mo.).

Triheptanoin can be obtained by the esterification of heptanoic acid and glycerol by any means known in the art. Triheptanoin is also commercially available through CondeaChemie GmbH (Witten, Germany) as Special Oil 107.

Unsaturated heptanoate can also be utilized in the present invention. In addition, substituted, unsaturated, and/or branched seven-carbon fatty acids which readily enter the mitochondrion without special transport enzymes can be utilized in the present invention. For example, 4-methylhexanoate, 4-methylhexenoate, and 3-hydroxy-4-methylhexanoate are broken down by normal b-oxidation to 2-methylbutyric acid with final degradation accomplished via the isoleucine pathway. Likewise, 5-methylhexanoate, 5-methylhexenoate, and 3-hydroxy-5-methylhexanoate are broken down by normal b-oxidation to isovaleric acid with final degradation accomplished via the leucine pathway.

Precursors of propionyl-CoA of the present invention can be administered orally, parenterally, or intraperitoneally. Preferably, it can be administered via ingestion of a food substance containing a precursor of propionyl-CoA such as triheptanoin at a concentration effective to achieve therapeutic levels. Alternatively, it can be administered as a capsule or entrapped in liposomes, in solution or suspension, alone or in combination with other nutrients, additional sweetening and/or flavoring agents. Capsules and tablets can be coated with sugar, shellac and other enteric agents as is known. Typically medicaments according to the invention comprise a precursor of propionyl-CoA, together with a pharmaceutically-acceptable carrier. A person skilled in the art will be aware of suitable carriers. Suitable formulations for administration by any desired route may be prepared by standard methods, for example by reference to well-known text such as Remington; The Science and Practice of Pharmacy.

In the following, the invention will be illustrated by means of the following examples as well as the figures.

FIGURE LEGENDS

FIG. 1: Partial least square (PLS) analyses of NMR spectra of plasma samples from HD patients with no or little signs of the disease and controls. Three groups of premanifest, early and mildly affected HD patients were constituted on the basis of their UHDRS scores, as described in the methods. The first and second components in the X space (NMR spectrum) are denoted PC[1] and PC[2] respectively. PLS score plots (PC[1]/PC[2]) of pair-wise compared groups show the greater variation within the NMR spectrum according to a priori classification with UHDRS. There is a clear separation between premanifest and early HD patients (a), as well as between early and mildly affected HD patients (b). Therefore, plasma NMR spectroscopy allows separation of HD patients at different stages of the disease. Despite some overlap, differentiation between controls and premanifest individuals is also observed (c).

Figure 2:
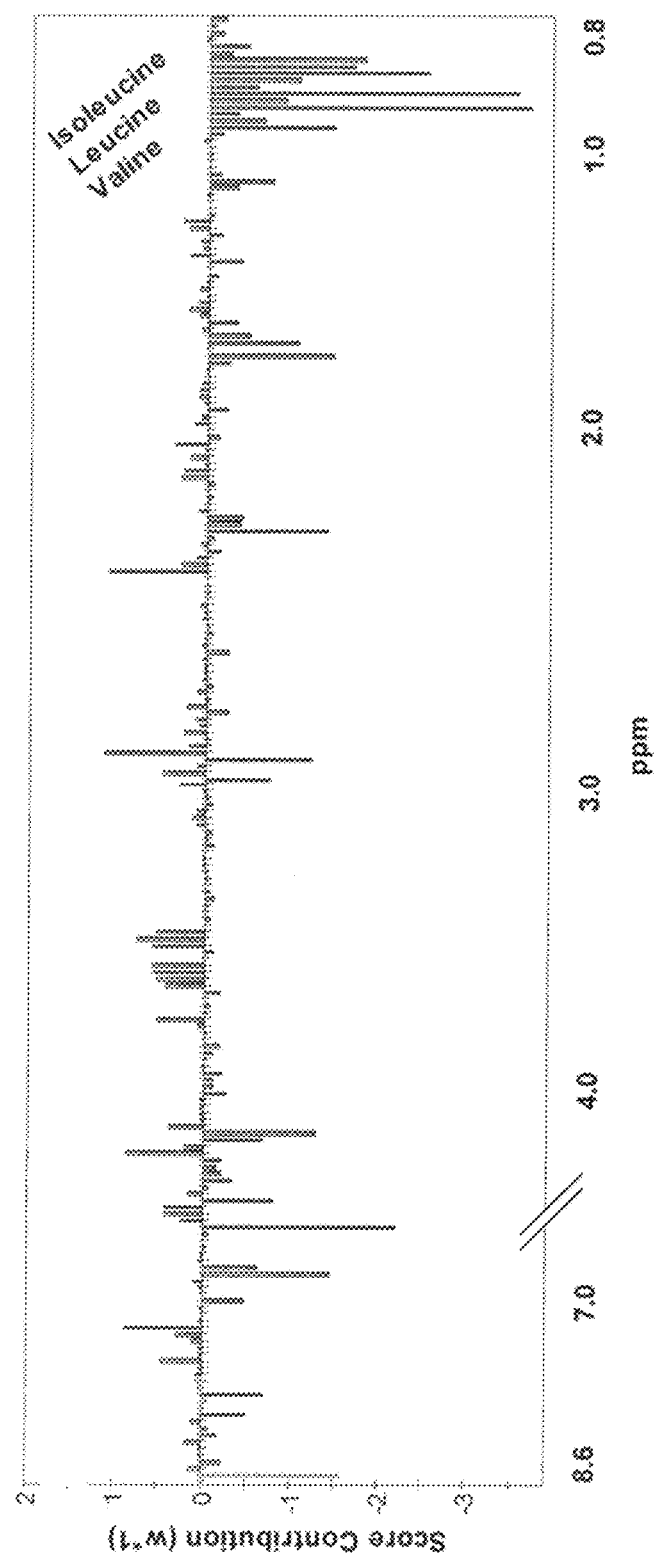

FIG. 2: Plasma relative concentrations of branched chain amino acids are responsible for separation between HD groups. PLS-contribution plot allows comparison between plasma metabolic profiles from early affected HD patients to premanifest carriers. NMR variables that have the greatest weight ($w^*_1$; scaled in units of standard deviation), therefore contributing most to the separation between HD groups, are decreased concentrations (>2SD) of metabolites located between 0.9 and 1.05 ppm: valine, leucine and isoleucine. The same contribution plot was obtained when comparing plasma metabolic profiles from mildly to early affected HD patients (data not shown).

Figure 3:
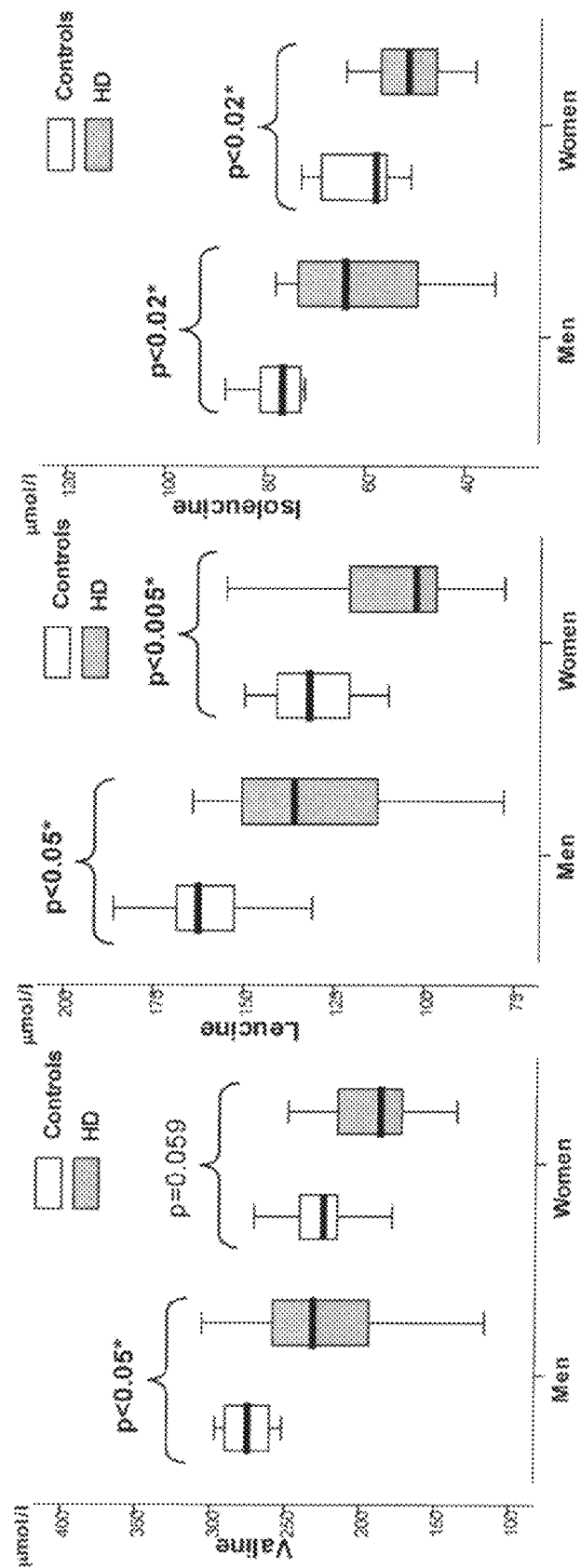

FIG. 3: The levels of branched chain amino acids are significantly different in HD patients and controls. The concentrations of valine, leucine and isoleucine in plasma were determined by ion exchange chromatography. Comparisons of means (ANOVA) were made between men or women with HD and their respective controls. In men, there is a significant decrease of valine, leucine and isoleucine in the HD group. In women, similar results are observed for leucine and isoleucine. Of note, in both men and women, the comparison of the standard deviations of valine, leucine and isoleucine values shows almost no overlap between the control and the HD groups.

Figure 4:
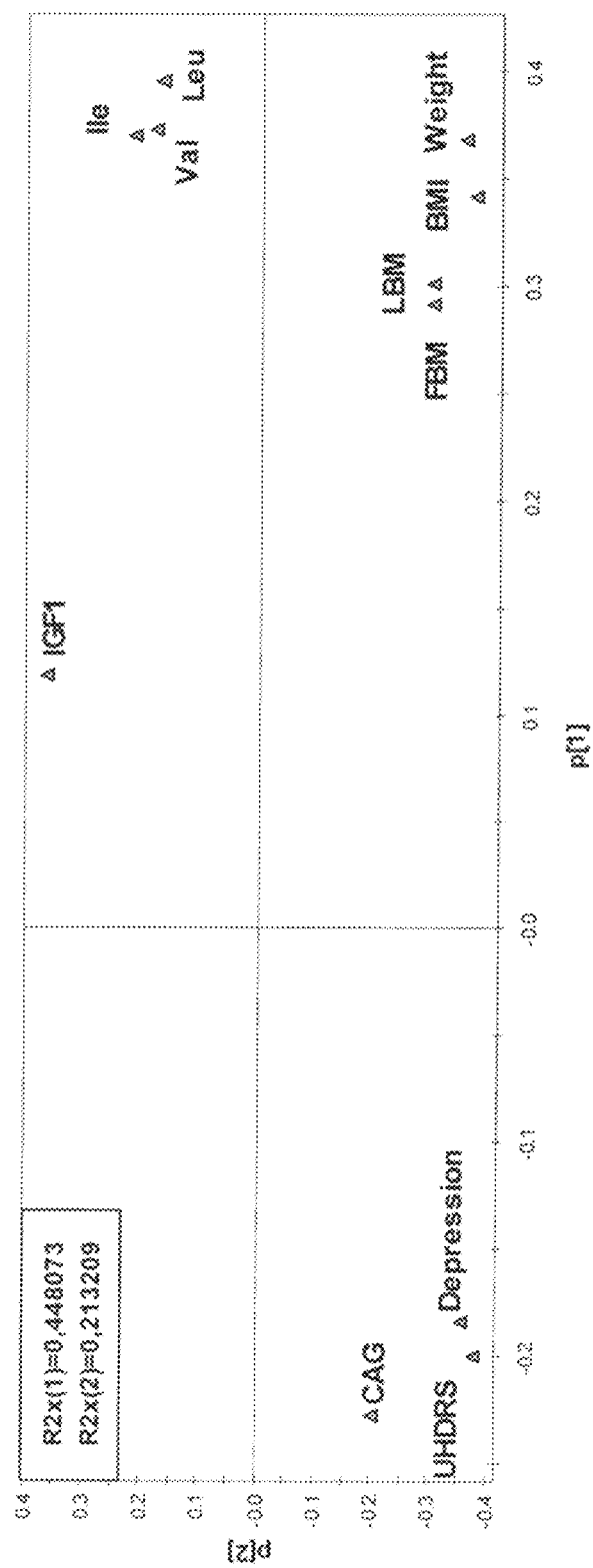

FIG. 4: Plasma branched chain amino acids are negatively correlated with disease progression in HD. Principal component analysis (PCA) loading plot shows the relative importance of each variable from the study and the correlation between these variables. The more the loading (p) of each variable diverges from zero, the more this variable is important in the explained variance of the given component (expressed by R2x). The explained variance of all data reach 44% in the first component and 22% in the second component. There is strong negative correlation between clinical markers (the size of the abnormal CAG repeat expansion, disease severity measured by the UHDRS and depression scores) and parameters associated with weight (weight, BMI, LBM and FBM for lean and fat body mass respectively). The BCAA, valine, leucine and isoleucine, are negatively correlated with disease progression and positively correlated with weight loss. Note that the number of CAG repeats are negatively correlated with BCAA values: the larger the repeat the lower the BCAA values (p=0.015 for valine, 0.018 for leucine and 0.020 for isoleucine).

FIG. 5: Diagram depicting the metabolic pathway of triheptanoin.

Figure 6:
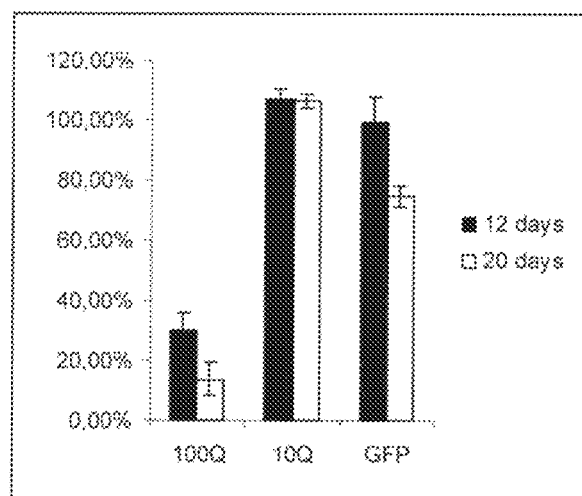

FIG. 6: Purkinje cell survival 12 days and 20 days following infection with the lentiviral vectors. 100Q: ATXN7T-100Q-GFP. 10Q: ATXN7T-10Q-GFP. GFP: control vector expressing GFP alone. The Purkinje cell survival is expressed as the percentage of Calbindin-positive cells in infected cultures compared to non-infected cultures. 12 days after infection by ATXN7T-100Q-GFP, Purkinje cell survival is reduced to ~30% and further decreases to ~15% after 20 days demonstrating the high and progressive neurotoxicity of the mutant protein, which is clearly distinct from the toxicity of the viral vector alone (GFP condition).

Figure 7:
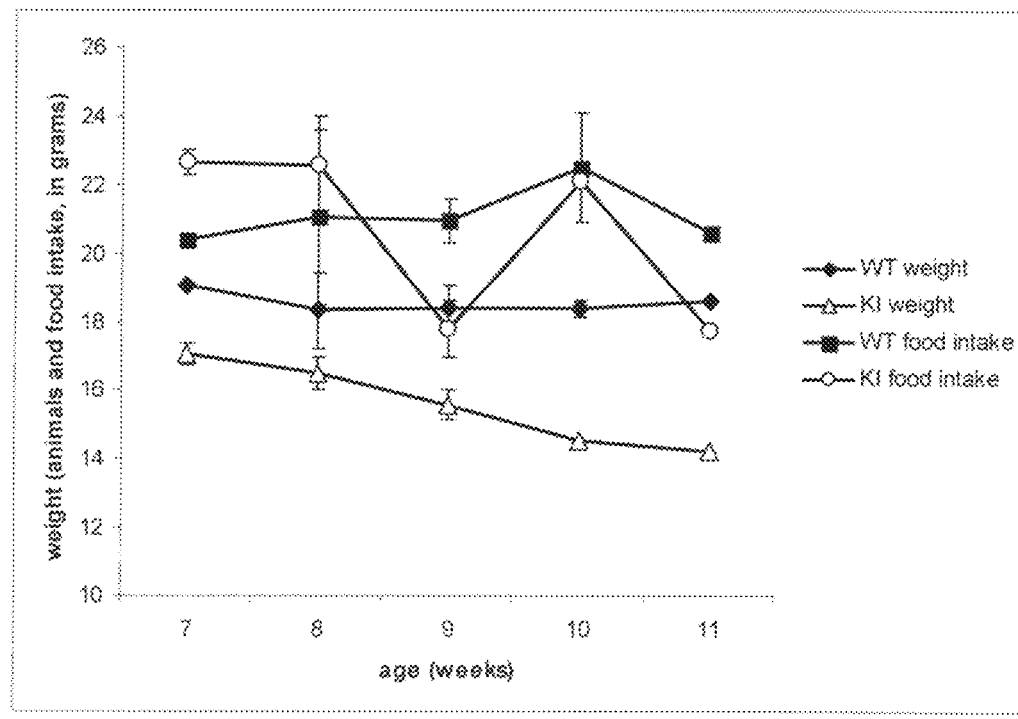

FIG. 7: Weight and food intake evolution of female knock-in mice (n=3) and female wild-type mice (n=3) from 7 to 11 weeks of age.

EXAMPLES

In the following description, all molecular biology experiments for which no detailed protocol is given are performed according to standard protocol.

Example 1: Identification of a Plasma Biomarker in Premanifest Carriers of Huntington Disease Indicating Early Energy Imbalance Abbreviations HD (Huntington disease), UHDRS (Unified Huntington disease rating scale), ppm (parts per million), PCA (principal components analysis), PLS (partial least square).
Abstract Huntington disease (HD) is an autosomal dominant neurodegenerative disorder in which an energy deficiency is thought to play a role. Patients consistently lose weight, although the reason for this is unknown. In view of the specific access to premanifest carriers in HD, we performed a multiparametric study in a group of 32 individuals with no sign or little of the disease compared to 21 controls. Weight loss was observed even in premanifest carriers in the HD group, although their caloric intake was higher. Inflammatory processes were ruled out, as well as primary hormonal dysfunction, including ghrelin and leptin balance. Proton nuclear magnetic resonance spectroscopy on plasma did, however, distinguish HD patients at different stages of the disease and premanifest carriers from controls. Differences between groups were attributable to low levels of the branched chain amino acids (BCAA), valine, leucine and isoleucine. We confirmed that BCAA levels were negatively correlated with weight loss and more importantly with disease progression. Levels of insulin growth factor type 1 (IGF1), which is regulated by BCAA, were also lower in the HD group than in controls. BCAA are, therefore, the first biomarkers identified in HD and offer new insights into an underlying early energy deficiency.
Results
Evidence of Early Hypercatabolism in HD Three groups were defined according to their UHDRS scores. There were 15 carriers of the mutation without any motor or cognitive signs of HD (UHDRS 0.5±1.0), 10 patients in an early stage of the disease (UHDRS 11.9±4.9) and 7 patients mildly affected (UHDRS 44.4±14.1) Weight loss during the last 5 years was significantly greater in the HD group than in controls (p<0.0001). The difference remained significant when men (p=0.002) and women (p=0.003) were analyzed separately. In spite of higher intake of calories, HD individuals and controls showed no different BMI. Importantly, in HD men, BMI was significantly lower than in controls, and total calories were even inversely correlated with weight (p=0.029) and lean body mass (p=0.004).

These observations confirm that weight balance is abnormal early in HD. Even in premanifest carriers, the nutritional pattern of HD patients differed from that of controls; they had significantly higher caloric intake (2195±495, n=15 versus 1665±305, n=21, p<0.001) and greater protein intake (85±24, n=15 versus 70±14, n=21, p=0.025). These observations clearly show hypercatabolism in the HD group, even in the very early stages of the disease. Relationship to the disease was not explained by common causes of hypercatabolism such as inflammation or classical endocrine dysfunctions. Indeed, ERS, CRP, serum interleukins 113 and 6 and serum fasting cortisol, T4L and TSH were similar in the HD and control groups. There was no glycosuria, and fasting blood glucose and insulin levels were in the normal range in the HD group.
Identification of Candidate Biomarkers by Plasma $^1$H NMR Spectroscopy (FIGS. 1 and 2)

PCA on plasma NMR spectra identified no outliers in both the control and HD dataset. PLS analyses could distinguish HD individuals at different stages of the disease, meaning that underlying plasma metabolites behaved differently. The difference between premanifest carriers and early HD was evident (FIG. 1a), and extended to more advanced stages of the disease (FIG. 1b). In addition, controls and premanifest carriers did not have the same metabolic profile, despite some overlap (FIG. 1c).

The spectral region that contributed to differences among the HD groups determined from PLS contribution plots is shown in FIG. 2. Plasma metabolic profile from early affected HD patients to premanifest carriers was compared, as well as from mildly to early affected HD patients. There was a significant (>2SD) decrease along with disease progression in the plasma concentrations of a group of variables from the buckets located between 0.9 to 1.05 ppm on the NMR spectrum. These peaks correspond to the branched chain amino acids (BCAA), valine, leucine and isoleucine. No other significant differences among the groups were detected in the spectra even though very small buckets (0.02 ppm) were analyzed. This indicates that a selective decrease in BCAA concentrations accompanies the progression of the disease, and even distinguishes premanifest carriers from both controls and early HD patients. Plasma BCAA levels appear, therefore, to be relevant biomarkers of HD.

Confirmation that BCAA are Affected in HD (FIGS. 3 and 4)

To confirm that BCAA are affected in HD, we also measured their concentrations in plasma by ion exchange chromatography. Valine, leucine and isoleucine levels were significantly lower in the HD group compared to controls (p=0.009, p<0.001 and p=0.002, respectively). In addition, the levels of each BCAA were significantly correlated with the observed weight loss in the patients (p=0.005, 0.002 and 0.014 respectively). More importantly, BCAA levels were negatively correlated with UHDRS values (p=0.017, <0.0001 and 0.003 respectively) in both men (p=0.035, 0.019 and 0.036 respectively) and women (p=0.007 for leucine and 0.01 for isoleucine). Although the BMI values of women with HD were similar to the controls, they had significantly lower leucine (p=0.002) and isoleucine (p=0.014) levels (FIG. 3). This indicates that lower BCAA levels are not only associated with weight balance, but more importantly with Huntington disease itself. Interestingly, the plasma levels of the three BCAA were significantly lower in patients at an early stage of the disease compared to premanifest carriers (p=0.042, 0.019 and 0.024 respectively). BCAA levels are, therefore, associated with disease onset, emphasizing that they can be used as reliable biomarkers in HD. When comparing premanifest carriers to controls, the plasma levels of valine (228±50 versus 245±44), leucine (130±24 versus 144±23) and isoleucine (62±12 versus 68±15) were lower in the former group, although not significantly. This is likely due to the heterogeneity of the premanifest group in which the estimated time to disease onset is expected to vary between individuals, so that the metabolic profile of some premanifest carriers can be similar to controls.

A multivariate PCA confirms that there is a strong negative correlation between clinical markers (abnormal CAG repeat expansion size, UHDRS scores, depression scores) and weight parameters (FIG. 4). Low BCAA values appear to be the strongest variables that are negatively correlated with HD and positively correlated with weight loss. The numbers of CAG repeats are also negatively correlated with BCAA values: the larger the repeat the lower the values (p=0.015 for valine, 0.018 for leucine and 0.020 for isoleucine).

The other metabolic markers (serum cholesterol and triglycerides, remaining amino acids and acylcarnitines in plasma, organic acids in urine) were similar in the HD group and in controls. IGF1 levels, however, were significantly lower in the HD group (p=0.011) and negatively correlated with UHDRS scores (p=0.004). IGF1 levels were also correlated with leucine (p=0.04) and isoleucine (p=0.02) levels, which was expected since IGF1 is regulated by BCAA. However, this has to be modulated by the fact that IGF1 levels are known to decrease with age, as observed in our HD cohort (p=0.002). The decrease in IGF1 levels was not associated with significant changes in other nutritional parameters (albumin, prealbumin, orosomucoid). There was no correlation either between IGF1 levels and parameters associated with weight (BMI, lean and fat body mass) or food intake.

Discussion

This is the first extended investigation of weight disorder in HD. We have shown that weight loss begins early in the disease, despite higher caloric intake, and is evident even in premanifest mutation carriers and those with little or no chorea. This hypercatabolism cannot be explained by common mechanisms like inflammation or altered endocrine functions, both of which have been incriminated in the pathophysiology of HD (Kremer et al. 1989; Pavese et al. 2006). Hypercatabolism in HD seems, therefore, to be part of the pathological process induced by the disease.

Our $^1$H NMR spectroscopy analysis shows that patients at different stages of HD can be distinguished from each other, and premanifest mutation carriers can be distinguished from controls, on the basis of their plasma levels of branched chain amino acids. The decrease in the levels of these amino acids correlated with weight loss in HD patients, but more importantly with the severity of the clinical impairment, i.e., with Huntington disease itself. This finding is supported by previous studies in which a decrease in plasma BCAA was documented in more severely affected HD patients (Perry et al. 1969; Phillipson and Bird 1977; Reilmann et al. 1995). The extensive metabolic screening we performed in combination with an independent technique confirmed that plasma BCAA were the only metabolites that differed between the HD group and controls. This difference existed regardless of sex and between patients at an early stage of the disease and premanifest carriers. Consequently, plasma BCAA can be considered as relevant biomarkers for Huntington disease. They should help to detect the onset of the disease and to monitor its progression in view of therapeutic trials. To our knowledge, this is the first accessible biomarker identified in Huntington disease and, more widely, the first peripheral biomarker evidenced in a neurodegenerative disorder.

Only few metabonomic studies have led to the identification of biomarkers that can be used routinely for the follow up of patients (Sabatine et al. 2005). Inter-individual variability is known to complicate such analyses in human body fluids, thus restricting metabonomic studies essentially to animal models (Wagner et al. 2006). Common experimental and analytical biases in humans include dietary intake, time of sample collection, sample conditioning and chemical shifts due to changes in pH (Cloarec et al. 2005; Teahan et al. 2006; Walsh et al. 2006). In the present study, each of these parameters was rigorously controlled. This probably explains the accuracy of our NMR findings.

The implication of BCAA in mitochondrial intermediary metabolism, both in brain and peripheral tissues, further supports an important role for energy deficit in HD. A reduction in ATP production was shown in brain of HD mice, including presymptomatic mice (Gines et al. 2003). A significant reduction in ATP levels and mitochondrial respiration was also evidenced in striatal cells of HD mice, although the respiratory chain complexes were not impaired (Milakovic and Johnson 2005). In HD patients, there is strong evidence for hypometabolism in the brain where glucose consumption is reduced, especially in the basal ganglia, even in presymptomatic mutation carriers (Grafton et al. 1992; Kuwert et al. 1993; Antonini et al. 1996). The underlying cause of this early energy deficit in HD brain is currently unknown, but impaired glycolysis (Browne and Beal 2004), citric acid cycle (Tabrizi et al. 1999) and/or oxidative phosphorylation (Milakovic and Johnson 2005) may be involved. Recently, mutated huntingtin was shown to decrease the expression of PGC-1α (peroxisome proliferators-activated receptor gamma coactivator-1α) in the striatum of HD mice and patients, through a CREB-dependent transcriptional inhibition (Cui et al. 2006). PGC-1α is a transcriptional coactivator that regulates key energetic metabolic pathways, both in the brain and peripheral tissues (Lin et al. 2005). The possible role of PGC-1α in HD was initially suspected from the observation of selective striatal lesions in the PGC-1α knockout mouse (Lin et al. 2004). Down-regulation of PGC-1α in HD striatum was then shown to affect mitochondrial energy metabolism, possibly by impairing oxidative phosphorylation (Cui et al. 2006). In addition, the inhibition of succinate dehydrogenase, by 3-nitropropionic acid or malonate, mimics HD neuropathology in mice (Klivenyi et al. 2004), indicating that a lack of substrates for the citric acid cycle and the respiratory chain is implicated in the energy deficit in HD brain. Importantly, mitochondrial oxidation of BCAA leads to the production of acetyl-CoA and succinyl-CoA, two key intermediates of the citric acid cycle. Insufficient caloric or protein intake was excluded in our study, as well as impairment of the BCAA oxidation pathway since organic acid levels in urine were normal. Therefore, the decrease in plasma BCAA observed in the HD group probably results from the activation of a compensatory mechanism to provide energy substrates to the citric acid cycle, as described in various cachexia-producing illnesses (Szpetnar et al. 2004; De Bandt and Cynober 2006). The correlation between decreased BCAA levels and weight loss in our study suggests that excessive mobilization and oxidation of BCAA to produce energy in muscle is associated with weight loss and reduced lean body mass. The observation of weight loss prior to neurocognitive decline suggests that neurological symptoms are exacerbated when substrates from the periphery become insufficient to compensate for the energy deficit in the HD brain. The normal rate of oxygen consumption recently observed after striatal infusion of succinate (Weydt et al. 2006) supports the idea that providing energy through an increase in both systemic and cerebral citric acid cycle intermediates may be a promising therapeutic approach in HD.

On the pathophysiological level, our study also showed that low plasma BCAA levels result in low IGF1 levels in the HD group compared to controls although they have a higher protein and caloric intake. The tight connection between IGF1 and essential amino acids has been extensively studied (Straus and Takemoto 1988; Harp et al. 1991; Thissen et al. 1994; Gomez-Merino et al. 2004). The availability of essential amino acids seems to have a greater effect on IGF1 gene expression than hormonal stimuli such as serum insulin concentrations (Maiter et al. 1989). IGF1 is also a more sensitive indicator of nutrient repletion than albumin, prealbumin or orosomucoide, as observed in our study. Interestingly, huntingtin is a substrate of the serine-threonine Akt pathway, which is activated by IGF1 (Humbert et al. 2002). Altered activation of the Akt pathway has been shown to decrease phosphorylation of the mutated huntingtin, resulting in an increased neuronal toxicity (Rangone et al. 2005). Low levels of IGF1 in HD patients might therefore provide an explanation of the alteration in Akt activation observed in HD cellular models. Consequently, increasing BCAA levels to correct the deficit in IGF1, should favor the phosphorylation of mutated huntingtin, thereby decreasing its toxicity.

In conclusion, the combination of a rigorous nutritional assessment and metabonomic tools has provided new insight into HD. We have demonstrated the existence of an early energy deficiency in this neurodegenerative disorder, reflected by weight loss. We have also identified the first reliable biomarker in Huntington disease. The evidence of decreased plasma BCAA levels in very early stages of HD highlights the possibility for therapies aimed at supplying a sufficient pool of acetyl-CoA to compensate for the early energy deficit.

Altogether, these data are supportive of a causative role for energy deficiency in Huntington's disease. Rather than a defect in the respiratory chain, low plasma BCAA levels indicate an energetic impairment in the Krebs cycle. Therefore, molecules selected for their ability to reverse this deficiency in mitochondrial ATP production should refill the pool of catalytic intermediates of the Krebs cycle. Dietary compounds such as triheptanoin have recently been used in human therapeutic trials for their ability to refill the pools of catalytic intermediates of the Kreb's cycle, a key energetic process called anaplerosis. Because of additional evidence for triheptanoin metabolites to cross the blood brain barrier, anaplerotic therapies represent promising molecules for reversing the energy deficiency associated with neurodegenerative diseases and thereby correcting some if not all clinical manifestations of these diseases.

Material and Methods

HD Patients, Premanifest Carriers and Controls

We included 32 individuals with abnormal CAG repeats expansions (>36) in the HD1 gene (19 women and 13 men) and 21 controls (13 women and 8 men). In the HD group, 15 were premanifest carriers who had before applied for predictive testing due to their risk for HD, 10 were at a very early stage of the disease and 7 had moderate signs of the disease. Controls were healthy volunteers in the same age range, unrelated to HD individuals. All participants were examined and blood samples were taken during a single visit to the reference centre for HD at the Salpêtrière Hospital (Paris). Patients, premanifest carriers and controls were enrolled in a clinical protocol authorized by the Assistance Publique des Hôpitaux de Paris (CRC 05129), and approved by the local ethics committee. Informed consent was obtained for all participants.

Determination of Weight Balance and Food Intake

Height and weight were recorded the day of the clinical examination. Weight loss was calculated by subtracting current weight from the weight of the patient 5 years before inclusion in the study. This information was obtained during the interview and was verified retrospectively from the patients' medical files. The body mass index (BMI) was obtained by dividing weight (in kilograms) by height (in meters) squared. Bioelectrical impedance (Tanita®) was measured to evaluate the lean mass and fat mass of all participants (Segal et al. 1988).

To determine food intake, HD patients at early stages, premanifest carriers and controls prospectively recorded their normal food consumption during 3 days preceding their examination. The accuracy of the 3-days record was verified one month later with a questionnaire assessing food intake over a 24-hours period that was sent to the homes of all participants. A professional dietician (CG) used these two documents to calculate mean total calories, and protein, lipid and sugar intake for both the HD and control groups using an automated system (Diaeta Software®).

Multiparametric Evaluation of Weight Balance

A standardized protocol was designed to thoroughly evaluate all possible causes of weight loss and to avoid biases related to food intake and circadian changes. It included sequentially: (i) a minimal 12 hours fast the night preceding the examination, (ii) and morning blood and urine collection at the same hour (9 am) Samples were stored on ice for immediate analyses or frozen at −80° C. for further analyses.

Standard analyses included blood cell count, blood and urine glucose, serum electrolytes, and basic nutritional parameters, such as serum cholesterol, triglycerides, albumin, prealbumin and orosomucoid. To refine the evaluation of nutrient repletion, serum insulin growth factor type 1 (IGF1) concentrations were measured using a specific immunoradiometric assay (IGF1 RIACT, Cis-Bio International, Gif-sur-Yvette, France). The three main axes involved in the regulation of weight balance were explored: inflammation, endocrine function and intermediary metabolism. The evaluation of inflammation included determination of the erythrocyte sedimentation rate (ESR) and quantification of C-reactive protein (CRP) and the serum interleukins IL1β and IL6 by ELISA (Diaclone, Besancon, France). Besides serum IGF1, the basic endocrine evaluation included measurements of fasting serum cortisol (at 9 am), tetraiodothyronine (T4L), thyroid stimulating hormone (TSH) and insulin (Elisa Access ultrasensitive insulin, Beckman Coulter, Roissy, France).

We explored intermediary metabolism through analysis of (i) plasma amino acids using ion exchange chromatography after coloration by ninhydrine (Aminotag, Geol), (ii) organic acids in urine by gas chromatography (GS Variant 3400) coupled to mass spectrometry (Ion trap, Saturn 2000, Variant) after extraction with ethyl acetate and derivation by silylation, (iii) the plasma acylcarnitines profile by tandem mass spectrometry (Applied Biosystem) with electrospray ionization (ESI) and FIA (flow injection analysis). Acylcarnitines were identified by using a precursor ion m/z 85 scan and quantified in MRM (multiple reaction monitoring) mode. Acetylcarnitine (C2-carnitine) levels were used to survey the fasting status of both HD individuals and controls (Costa et al. 1999).

$^1$H Nuclear Magnetic Resonance Spectroscopy (NMR) on Plasma

Plasma samples were prepared for $^1$H NMR spectroscopy with minimal handling. Plasma samples were deproteinized using a 10 kDa filter (Nanosep, Omega) to avoid interference from high molecular weight species such as lipoproteins. Before use, the filter was washed twice with water by centrifugation to remove glycerol. A 100 µl aliquot of 3.89 mM [trimethylsilyl]-2,2,3,3-tetradeuteropropionic acid in $^2$H$_2$O (TSP-$^2$H$_2$O, Aldrich) was added to 500 µl of the ultrafiltrate, providing a chemical shift reference (δ=0.00 ppm), a concentration reference and a deuterium lock signal. The pH of the ultrafiltrate was adjusted to 2.50±0.05 with concentrated HCl. Finally, 500 µl of the sample was placed in a 5 mm NMR tube (Wilmad Royal Imperial). The $^1$H NMR spectra were determined on an Avance-500 SB spectrometer (Bruker, France) equipped with a 5 mm BBI (broadband inverse) probe; samples were not spun. Spectra were collected at 25° C. and consisted in 32K data points with a spectral width of 6,000 Hz and a total acquisition times of 27 min. A 90° radiofrequency pulse, following a water signal presaturation of 10 s, was used for each 128 scans. Shimming of the sample was performed automatically on the deuterium signal. The resonance line widths for TSP and metabolites were <1 Hz. Before a Fourier transformation into 64K data points, a sine-bell squared filter (SSB=2) was used to reduce noise. The phase and the baseline were corrected manually using the spectrometer software (X-Win NMR 3.5, Bruker, France). NMR spectra were first analyzed individually in order to detect abnormal signals—i.e. treatment or special food—that could further interfere with global analyses. For statistical analyses, spectra were data reduced in numerical format by integrating spectral regions (buckets) every 0.02 ppm and scaled to the total intensity of the spectrum with Amix 3.6.8 software (Bruker Analytische Messtechnik, Germany) from 0.8 to 8.6 ppm, the water peak area being excluded from each spectrum (4.4 to 5.2 ppm). Accordingly, each bucket from the NMR spectrum corresponded to a single variable.

Statistical Analyses

Metabonomic studies consist in multivariate statistical analyses, e.g. principal components analysis (PCA) and partial least squares analysis (PLS), with as many components as variables. Multivariate analyses of the data obtained by NMR spectroscopy were performed with Simca-P® 11.0 software (Umetrics, Sweden). For PCA and PLS, unit variance scaled data were used to ensure the inclusion of metabolites present in both high and low concentrations. Each variable was mean centered and computed as 1/SD$_j$, standard deviation of variable j computed around the mean. PCA considers each bucket from the NMR spectrum as an X variable and was therefore used to discern the presence of inherent similarities between spectral profiles and to identify outliers. PLS is a regression extension of PCA and best describe the variation within the data according to a priori classification, corresponding to a Y variable, which was the UHDRS score in our study. PLS was used to identify principal components maximizing the covariance between all X (NMR spectrum) and Y (UHDRS) variables. The greatest dispersion of the spectral profiles is usually best observed in the two first components of the analyses. The first and second components in the X space (NMR spectrum) were denoted PC[1] and PC[2] respectively. Therefore, PLS score plot (PC[1]/PC[2]) of pair-wise compared groups displayed the greater variation within the NMR spectrum according to UHDRS. The validity of each component was obtained by cross validation. Contribution plot was then analyzed in order to determine the respective weight of variables contributing most to the separation between groups.

For comparison of means, ANOVA or non-parametric tests when appropriate, were used (SPSS® software). Since our study was based on a multiparametric approach, we also performed PCA to search for possible correlations between the different parameters that were analyzed (Simca-P® software).

REFERENCES

Antonini A, Leenders K L, Spiegel R, et al. (1996). "Striatal glucose metabolism and dopamine D2 receptor binding in asymptomatic gene carriers and patients with Huntington's disease." Brain 119 (Pt 6): 2085-95.

Browne S E and Beal M F (2004). "The energetics of Huntington's disease." Neurochem Res 29 (3): 531-46.

Cloarec O, Dumas M E, Trygg J, et al. (2005). "Evaluation of the orthogonal projection on latent structure model limitations caused by chemical shift variability and improved visualization of biomarker changes in $^1$H NMR spectroscopic metabonomic studies." Anal Chem 77 (2): 517-26.

Costa C C, de Almeida I T, Jakobs C, Poll—The B T and Duran M (1999). "Dynamic changes of plasma acylcarnitine levels induced by fasting and sunflower oil challenge test in children." Pediatr Res 46 (4): 440-4.

Cui L, Jeong H, Borovecki F, Parkhurst C N, Tanese N and Krainc D (2006). "Transcriptional repression of PGC-1alpha by mutant huntingtin leads to mitochondrial dysfunction and neurodegeneration." Cell 127 (1): 59-69.

De Bandt J P and Cynober L (2006). "Therapeutic use of branched-chain amino acids in burn, trauma, and sepsis." J Nutr 136 (1 Suppl): 308S-13S.

Gines S, Seong I S, Fossale E, et al. (2003). "Specific progressive cAMP reduction implicates energy deficit in presymptomatic Huntington's disease knock-in mice." Hum Mol Genet. 12 (5): 497-508.

Gomez-Merino D, Chemaoui M, Drogou C and Guezennec C Y (2004). "Influence of energy deficiency on the insulin-like growth factor I axis in a military training program." Horm Metab Res 36 (7): 506-11.

Grafton S T, Mazziotta J C, Pahl J J, et al. (1992). "Serial changes of cerebral glucose metabolism and caudate size in persons at risk for Huntington's disease." Arch Neurol 49 (11): 1161-7.

Harp J B, Goldstein S and Phillips L S (1991). "Nutrition and somatomedin. XXIII. Molecular regulation of IGF-I by amino acid availability in cultured hepatocytes." Diabetes 40 (1): 95-101.

Humbert S, Bryson E A, Cordelieres F P, et al. (2002). "The IGF-1/Akt pathway is neuroprotective in Huntington's disease and involves Huntingtin phosphorylation by Akt." Dev Cell 2 (6): 831-7.

Klivenyi P, Starkov A A, Calingasan N Y, et al. (2004). "Mice deficient in dihydrolipoamide dehydrogenase show increased vulnerability to MPTP, malonate and 3-nitropropionic acid neurotoxicity." J Neurochem 88 (6): 1352-60.

Kremer H P, Roos R A, Frolich M, Radder J K, Nieuwenhuijzen Kruseman A C, Van der Velde A and Buruma O J (1989). "Endocrine functions in Huntington's disease. A two-and-a-half years follow-up study." J Neurol Sci 90 (3): 335-44.

Kuwert T, Lange H W, Boecker H, et al. (1993). "Striatal glucose consumption in chorea-free subjects at risk of Huntington's disease." J Neurol 241 (1): 31-6.

Lin J, Handschin C and Spiegelman B M (2005). "Metabolic control through the PGC-1 family of transcription coactivators." Cell Metab 1 (6): 361-70.

Lin J, Wu P H, Tarr P T, et al. (2004). "Defects in adaptive energy metabolism with CNS-linked hyperactivity in PGC-1alpha null mice." Cell 119 (1): 121-35.

Maiter D, Fliesen T, Underwood L E, Maes M, Gerard G, Davenport M L and Ketelslegers J M (1989). "Dietary protein restriction decreases insulin-like growth factor I independent of insulin and liver growth hormone binding." Endocrinology 124 (5): 2604-11.

Milakovic T and Johnson G V (2005). "Mitochondrial respiration and ATP production are significantly impaired in striatal cells expressing mutant huntingtin." J Biol Chem 280 (35): 30773-82.

Pavese N, Gerhard A, Tai Y F, et al. (2006). "Microglial activation correlates with severity in Huntington disease: a clinical and PET study." Neurology 66 (11): 1638-43.

Perry T L, Diamond S, Hansen S and Stedman D (1969). "Plasma-aminoacid levels in Huntington's chorea." Lancet 1 (7599): 806-8.

Phillipson O T and Bird E D (1977). "Plasma glucose, non-esterified fatty acids and amino acids in Huntington's chorea." Clin Sci Mol Med 52 (3): 311-8.

Rangone H, Pardo R, Colin E, Girault J A, Saudou F and Humbert S (2005). "Phosphorylation of arfaptin 2 at Ser260 by Akt Inhibits PolyQ-huntingtin-induced toxicity by rescuing proteasome impairment." J Biol Chem 280 (23): 22021-8.

Reilmann R, Rolf L H and Lange H W (1995). "Decreased plasma alanine and isoleucine in Huntington's disease." Acta Neurol Scand 91 (3): 222-4.

Sabatine M S, Liu E, Morrow D A, et al. (2005). "Metabolomic identification of novel biomarkers of myocardial ischemia." Circulation 112 (25): 3868-75.

Segal K R, Van Loan M, Fitzgerald P I, Hodgdon J A and Van Itallie T B (1988). "Lean body mass estimation by bioelectrical impedance analysis: a four-site cross-validation study." Am J Clin Nutr 47 (1): 7-14.

Straus D S and Takemoto C D (1988). "Regulation of albumin mRNA in H4 rat hepatoma cells by the availability of essential amino acids." Biochim Biophys Acta 972 (1): 33-6.

Szpetnar M, Pasternak K and Boguszewska A (2004). "Branched chain amino acids (BCAAs) in heart diseases (ischaemic heart disease and myocardial infarction)." Ann Univ Mariae Curie Sklodowska [Med] 59 (2): 91-5.

Tabrizi S J, Cleeter M W, Xuereb J, Taanman J W, Cooper J M and Schapira A H (1999). "Biochemical abnormalities and excitotoxicity in Huntington's disease brain." Ann Neurol 45 (1): 25-32.

Teahan O, Gamble S, Holmes E, Waxman J, Nicholson J K, Bevan C and Keun H C (2006). "Impact of analytical bias in metabonomic studies of human blood serum and plasma." Anal Chem 78 (13): 4307-18.

Thissen J P, Ketelslegers J M and Underwood L E (1994). "Nutritional regulation of the insulin-like growth factors." Endocr Rev 15 (1): 80-101.

Wagner S, Scholz K, Donegan M, Burton L, Wingate J and Volkel W (2006). "Metabonomics and biomarker discovery: LC-MS metabolic profiling and constant neutral loss scanning combined with multivariate data analysis for mercapturic acid analysis." Anal Chem 78 (4): 1296-305.

Walsh M C, Brennan L, Malthouse J P, Roche H M and Gibney M J (2006). "Effect of acute dietary standardization on the urinary, plasma, and salivary metabolomic profiles of healthy humans." Am J Clin Nutr 84 (3): 531-9.

Weydt P, Pineda V V, Torrence A E, et al. (2006). "Thermoregulatory and metabolic defects in Huntington's disease transgenic mice implicate PGC-1alpha in Huntington's disease neurodegeneration." Cell Metab 4 (5): 349-62.

Example 2: Triheptanoin Therapy of HD Mouse Models

Aims of the Study

A pilot study is conducted to test the effect of dietary triheptanoin therapy versus control diet on selected strains of HD R6/2 mice (Mangariani 1996, Cell 87: 493-506, Kosinski 1999, Neuroreport 10: 3891-6). The study includes (i) measuring rates of cerebral anaplerosis from heptanoate and brain ATP in R6/2 mice of different ages and in control mice in order to demonstrate the ability of triheptanoin metabolites to cross the blood brain barrier of R6/2 mice and to reverse central energy deficit; (ii) assessing the therapeutic efficacy of triheptanoin by accurate behavioral testing, in vivo brain microdialysis (to assay neurotransmitters, triheptanoin metabolites, and BCAA) and neuropathological examination; (iii) metabolomic analyses on mouse plasma and urine.

Research Methods

R6/2 and control mice, on triheptanoin-enriched and control diets, are infused sequentially—at 4, 8 and 12 weeks—with various doses of $[5,6,7-^{13}C_3]$heptanoate (by gavage or by intravenous infusion) for 1 hr before brain sampling, in order to follow the kinetics of anaplerosis in the brain (using the assay of anaplerotic CoA esters). The concentrations of ATP, ADP, and AMP are assayed in all brain samples, as well as in muscle of R6/2 mice. We are also assessing the concentration and labeling pattern of neurotransmitters generated by anaplerosis (GABA, glutamate) to determine whether the brain is deficient in these compounds and whether anaplerotic therapy improves these parameters. Brain tissues are be stored at −70° C. in view of possible additional analyses (like measurement of oxidative stress).

Behavioral analyses include (i) open field activity monitoring using the TruScan system at 4, 8 and 12 weeks; (ii) RotaRod analysis performed using the AccuScan system equipped with a shockable floor at 6 and 12 weeks; (iii) and the Morris Water Maze, the most popular task in behavioral neuroscience used to assess spatial learning and memory at 12 weeks. Other primary endpoints from the study are weight loss and survival.

As both HD patients and genetic mouse models of HD manifest a presymptomatic loss of DA receptors, a dysfunctional dopaminergic neurotransmission may be involved in early HD presentation. More recent studies have shown that DA release is severely compromised in R6/2 mice (Johnson 2006, J Neurochem 97: 737-46). Accordingly, a first group of animals is sacrificed at 12 weeks by cervical dislocation for neurotransmitters analyses. Blood are collected and brain tissue are rapidly removed and dissected on ice into the following regions: striatum, hippocampus, frontal cortex, posterior cortex, cerebellum, and midbrain. These regions are dissected for both left and right hemispheres of the brain. All right side regions are processed for analysis of DA, 5-hydroxytryptophane (5-HT) and norepinephrine (NE) and related metabolites (3-dihydrophenylacetic acid, homovalinic acid, 3-methoxytyramine and 5-hydroxyindolacetic acid) by HPLC with electrochemical detection. Acetylcholine (Ach) is also measured in frontal posterior cortex tissue by HPLC with electrochemical detection. Branched chain amino acids is measured by HPLC and triheptanoin metabolites by mass spectrometry. Neuropathology, and especially nuclear neuronal inclusions, is performed on the left side regions. At 12 weeks, a second group of animals is prepared for in vivo microdialysis to monitor in-vivo release of DA, 5-HT by potassium and Ach release by scopolamine in the striatum. Changes in the extracellular concentrations of DA, 5-HT and Ach is compared by three ways ANOVA (time×genotype×diet) with repeated measures.

Sequential analyses of plasma and urine samples from R6/2 and control mice at 4, 8 and 12 weeks are also perfomed with both NMR spectroscopy and mass spectrometry. This aims the detection of triheptanoin metabolites (propionyl and pentanoyl-CoA derivatives) in body fluids from treated mice. The comparison of the metabolic profile from R6/2 and control mice on control diet, by multivariate data statistical analyses, can possibly confirm the implication of BCAA in the pathophysiology of R6/2 mice, as evidenced in HD premanifest carriers and patients, and partially suggested in previous metabolomic study in R6/2 mice (Underwood 2006, Brain 129: 877-8). More importantly, the comparison of the metabolic profile from treated versus non-treated R6/2 mice can assess whether triheptanoin can lead to the correction of such hypercatabolic profiles.

Example 3: Therapy of Spinocerebellar Ataxia 7 (SCA7)

1/ In Vitro Trial

To create a simplified model of SCA7 in vitro we used primary cultures of dissociated cerebellar cells because lesion of the cerebellum, particularly the Purkinje cell (PC) layer, accounts for the ataxia phenotype in patients with SCA7. Our cerebellar cell cultures were composed of glial cells and neurons, 5 to 10% of which expressed calbindin (CaBP) identifying them as PC. To examine the effects of mutant ATXNT7 on PC survival, the cells were infected at DIV1 (1st Day In Vitro) with lentiviral vectors carrying truncated forms of normal and mutant ataxin 7 (ATXN7T: amino acids 1-232) fused to GFP (ATXN7T-10Q-GFP, ATXN7T-100Q-GFP). These lentiviral vectors allowed efficient expression of these proteins in about 90% of neurons, including Purkinje cells. Infection by ATXN7T-100Q-GFP led to massive neuronal loss, almost exclusively in Purkinje neurons (~85% of Purkinje cell death versus ~20% loss of other neurons), thus reproducing one of the major features of the human disease (FIG. 6).

This model is used to assess the ability of anaploretic molecules to rescue Purkinje cells infected by ATXN7T-100Q-GFP. Two compounds are tested: the 3-ketovalerate and the 3-hydroxyvalerate, which are both be directly incorporated by the cells in culture. These molecules are added in the culture medium on the same day when the cells are infected and half of the medium is replaced every 4 days. The cultures are maintained for 20 days and the potential rescue of Purkinje cells is quantified as described above.

2/ In Vivo Experiments

We chose to use the SCA7 knock-in mouse model developed in the group of H. Y. Zoghbi (Yoo 2003 Neuron, 37: 383-401), which expresses ATXN7 with 266 glutamines at endogenous levels in the proper spatio-temporal pattern. Mouse Sca7 is highly homologous to human SCA7, with 88.7% identity at the protein level. Sca7$^{266Q/5Q}$ mice reproduce features of infantile SCA7, which is characterized by a more rapid progression and a broader spectrum of phenotypes than the adult-onset disease. From 5 weeks of age, these mice develop progressive weight loss, ptosis, visual impairment, tremor, ataxia, muscle wasting, kyphosis and finally die at around 14-19 weeks of age. Sca7$^{266Q/5Q}$ mice manifested coordination impairment in the rotarod test by 5 weeks. By 8-9 weeks, gait ataxia is apparent and motor coordination further deteriorates. As in patients, neuropathological studies revealed progressive NIs formation in many brain regions. Although no neuronal loss is observed in the brain, Purkinje cells that are one of the most commonly affected cells in SCA7, have a decreased body cell size.

a—Metabolic Study of the SCA7 Knock-in Mice

Similarly to patients with HD or SCA7, the SCA7 knock-in mice show a severe progressive weight loss already significant at the onset of the motor phenotype. A protocol has been set up to measure food and beverage intake in correlation with weight evolution of these mutant mice compared to wild-type ones. This protocol is tested on a group of 3 knock-in females and 3 wild-type females from the same litters. The animals are kept one per cage and they are given a definite amount of food and beverage. Then, their intake and their weight are measured four times a week. Preliminary results show that this procedure is efficient to evidence progressive weight loss and food intake evolution (FIG. 7). Soon after onset (7-8 weeks) but before serious motor deterioration (8-9 weeks) food intake from mutant animals is higher than in wild-type although there are already lighter. These data are in favour of the hypothesis of a hypermetabolic state during the early phases of the phenotype. After 8-9 weeks, the locomotor impairment is already so disabling that the mutant mice probably can't reach the food as easily as the wild-type ones.

b—Microarray Analysis of Early Transcriptional Modifications

Metabolic impairment in HD and other related diseases have been proposed to result from dysregulation of major metabolic pathways at the transcriptional level (Mochel 2007 PLoS ONE, 2(7): e647; Cui 2006 Cell 127: 59-69). Considering the function of the ATXN7 protein and the early transcriptional abnormalities previously evidenced in SCA7 and other polyglutamine disease, the transcriptome of the cerebellum of 4-5 knock-in mice versus 4-5 wild-type mice is analysed at two early stages before onset (post-natal day 10 and post-natal day 22) and one late symptomatic stage (11 weeks of age).

Example 4: Evaluation of the Potential Benefit and Safety of Anaplerotic Therapy in Huntington Disease (HD)

A 5-days preclinical trial with triheptanoin in 6 HD affected patients is conducted. This short-term protocol is as follows:
1. Day 1: (i) an extended neurological and general clinical examination; (ii) a global metabolic workup (blood and urine samples) to have an overview of the metabolic profile of HD patients at baseline; (iii) a skin biopsy to test in vitro the ability of triheptanoin to generate energy from the Krebs cycle and the respiratory chain; (iv) the measurement of 5'-AMP-activated protein kinase (5'AMPK) activity in patients' fibroblasts, as a reflection of the levels of intracellular energy metabolism; and (v) a $^{31}$P-NMR spectroscopy on patients' muscle in order to assess their skeletal muscle ATP production.
2. Day 2: an oral loading test of a meal enriched with triheptanoin, together with urine and blood samples before and after meal to determine:
   measurements of triheptanoin metabolites, through plasma acylcarnitines profile and urine organic acids (Roe et al. 2002), to ensure that triheptanoin is properly metabolized in HD patients;
   analyses of mitochondrial redox status, through the ratio of lactate to pyruvate and 3-hydroxybutyrate to acetoacetate (Mochel et al. 2005), to assess in vivo the ability of triheptanoin to generate energy from the Krebs cycle without overloading the respiratory chain.
3. On days 3, 4 and 5: the pursuit of a diet enriched with triheptanoin to determine if a protein sparing effect occurs, i.e. the normalization of the plasma branched chain amino acids (BCAA) and serum IGF1 levels, and/or the elevation of urinary urea. Clinical examination attempts to identify acute effects on the systemic energy deficiency (muscle strength, motor function) associated with HD. In addition, patients undergo a second muscle $^{31}$P-NMR spectroscopy in order to evidence a possible short-term effect of triheptanoin on patients' peripheral energy metabolism.

Study Design

On the first day of admission, HD patients are examined. Motor dysfunction is evaluated with the Unified Huntington disease rating scale, UHDRS (Siesling et al. 1998), and a total functional capacity score, TFC (Marder et al. 2000). General health condition is also recorded, in particular history of dysfunction of the digestive tract. Before lunch, blood and urine samples are collected. Standard analyses are performed (blood cell count, blood clotting factors, blood and urine glucose, serum electrolytes), as well as a global metabolic workup including plasma redox status (lactate, pyruvate, acetoacetate, 3-hydroxybutyrate), plasma amino acids and acylcarnitines, and urine organic acids as described (Mochel et al. 2005). In the absence of blood clotting dysfunction, a skin biopsy is performed. A simple functional test using propionate labelled with $C^{14}$ is further performed in cultured fibroblasts (Benoist et al. 2001). Propionate is one of the main anaplerotic products of triheptanoin, and is incorporated into protein providing that enough ATP is produced from the Krebs cycle and the respiratory chain. The normal rate of protein synthesis, after incorporation of $C^{14}$-propionate, in HD cells therefore reflect the integrity of the respiratory chain in HD, as well as the possibility to generate energy from the Krebs cycle through the anaplerotic pathway. The activity of 5'-AMPK, which senses changes in the cellular energy state, is also determined in patients' fibroblasts (Chou et al. 2005), in order to evidence a peripheral deficit in intracellular energy metabolism. In addition, oxidative mitochondrial metabolism is specifically assessed by muscle $^{31}$P-NMR spectroscopy using data collected at the end of a given exercise and during the following recovery (Lodi et al. 2000).

On the second day, HD patients ingest a loading dose of triheptanoin (1 g/Kg). For convenience, and better digestive tolerance, triheptanoin is usually administrated together with a dairy product. Repeated blood samples are collected before and, sequentially, after meal (30, 60, 90, 120 and 180 minutes after triheptanoin ingestion) for assessment of redox status and acylcarnitines profile. Urine is also collected before and after the triheptanoin load (90 and 180 minutes) for analyses of organic acids.

On the next 3 following days, HD patients pursue an isocaloric diet enriched with triheptanoin (1 g/Kg/day divided in 3 to 4 meals). Fasting plasma BCAA, serum IGF1 and urinary urea are analyzed daily and neurological examination is repeated with UHDRS and TFC scoring. On day 5, muscle $^{31}$P-NMR spectroscopy is repeated in order to determine the relative concentrations of inorganic phosphate, phosphocreatine and ATP levels after triheptanoin administration.

Patient Selection Criteria

This study involves 6 patients with abnormal CAG repeats expansions (>36) in the HD1 gene, with regular medical and psychological follow-up. The selection of patients is based on:
  UHDRS score ranging 15 and 50, corresponding to patients at an early to moderate stage of the disease, in order to facilitate the compliance of patients to dietary treatment;
  low levels of plasma BCAA, in order to search for a raise in these amino acids under triheptanoin treatment.
Informed consent is obtained for all participants.

REFERENCES

Benoist J F, Acquaviva C, Callebaut I, et al. (2001). "Molecular and structural analysis of two novel mutations in a patient with mut(−) methylmalonyl-CoA deficiency." Mol Genet Metab 72 (2): 181-4.

Chou S Y, Lee Y C, Chen H M, et al. (2005). "CGS21680 attenuates symptoms of Huntington's disease in a transgenic mouse model." J Neurochem 93 (2): 310-20.

Lodi R, Schapira A H, Manners D, Styles P, Wood N W, Taylor D J and Warner T T (2000). "Abnormal in vivo skeletal muscle energy metabolism in Huntington's disease and dentatorubropallidoluysian atrophy." Ann Neurol 48 (1): 72-6.

Marder K, Zhao H, Myers R H, et al. (2000). "Rate of functional decline in Huntington's disease. Huntington Study Group." Neurology 54 (2): 452-8.

Mochel F, DeLonlay P, Touati G, et al. (2005). "Pyruvate carboxylase deficiency: clinical and biochemical response to anaplerotic diet therapy." Mol Genet Metab 84 (4): 305-12.

Roe C R, Sweetman L, Roe D S, David F and Brunengraber H (2002). "Treatment of cardiomyopathy and rhabdomyolysis in long-chain fat oxidation disorders using an anaplerotic odd-chain triglyceride." J Clin Invest 110 (2): 259-69.

Siesling S, van Vugt J P, Zwinderman K A, Kieburtz K and Roos R A (1998). "Unified Huntington's disease rating scale: a follow up." Mov Disord 13 (6): 915-9.

Throughout this application, various references describe the state of the art to which this invention pertains. The disclosures of these references are hereby incorporated by reference into the present disclosure.

The invention claimed is:

1. A method of treating a polyglutamine disease, the method comprising administering to a patient in need of such treatment a composition comprising at least one precursor of propionyl-CoA in an amount effective for treating said polyglutamine disease in said patient, wherein the precursor of propionyl-CoA is selected from the group consisting of triheptanoin, heptanoic acid, and heptanoate.

2. The method according to claim 1, wherein the polyglutamine disease is Huntington disease.

3. The method according to claim 1, wherein the precursor of propionyl-CoA is triheptanoin.

4. The method according to claim 1, wherein the precursor of propionyl-CoA is administered via ingestion of a food substance containing said precursor of propionyl-CoA.

5. The method according to claim 2, wherein the precursor of propionyl-CoA is triheptanoin.

6. The method according claim 2, wherein the precursor of propionyl-CoA is administered via ingestion of a food substance containing said precursor of propionyl-CoA.

7. The method according to claim 2, wherein the patient has been identified as having significantly lower plasma levels of at least one branched chain amino acid (BCAA) as compared to a control.

8. The method according to claim 7, wherein the BCAA is selected from valine, leucine, and isoleucine.

* * * * *